(12) United States Patent
Yahagi et al.

(10) Patent No.: US 8,187,271 B2
(45) Date of Patent: May 29, 2012

(54) ENDOSCOPIC INSTRUMENT

(75) Inventors: Naohisa Yahagi, Tokyo (JP); Tsutomu Nakamura, Tokyo (JP); Keita Suzuki, Tokyo (JP); Koichi Kawashima, Tokyo (JP); Shunsuke Motosugi, Hirosaki (JP)

(73) Assignees: Naohisa Yahagi, Tokyo (JP); Olympus Medical Systems Corp., Tokyo (JP)

( * ) Notice: Subject to any disclaimer, the term of this patent is extended or adjusted under 35 U.S.C. 154(b) by 1070 days.

(21) Appl. No.: 12/108,859

(22) Filed: Apr. 24, 2008

(65) Prior Publication Data

US 2008/0269558 A1    Oct. 30, 2008

(30) Foreign Application Priority Data

Apr. 27, 2007 (JP) ................... P2007-119305

(51) Int. Cl.
*A61B 18/14* (2006.01)
(52) U.S. Cl. .................. 606/46; 606/41; 600/106
(58) Field of Classification Search .......... 606/41–49, 606/181
See application file for complete search history.

(56) References Cited

U.S. PATENT DOCUMENTS

| 4,222,380 | A | * | 9/1980 | Terayama | ............ 604/115 |
|---|---|---|---|---|---|
| 4,708,137 | A | | 11/1987 | Tsukagoshi | |
| 6,193,717 | B1 | | 2/2001 | Ouchi | |
| 7,731,714 | B2 | * | 6/2010 | Miyajima et al. | ............ 606/46 |
| 8,048,073 | B2 | * | 11/2011 | Nakamura et al. | ............ 606/46 |
| 2003/0060842 | A1 | | 3/2003 | Chin et al. | |
| 2004/0172018 | A1 | | 9/2004 | Okada | |
| 2004/0210284 | A1 | | 10/2004 | Okada | |
| 2006/0276784 | A1 | | 12/2006 | Miyajima et al. | |
| 2007/0088354 | A1 | | 4/2007 | Sugita | |

FOREIGN PATENT DOCUMENTS

| JP | 61-191012 | 11/1986 |
|---|---|---|
| JP | 4-329944 | 1/1992 |

(Continued)

OTHER PUBLICATIONS

Korean Application No. 10-2008-38588 Notice of Allowance dated May 31, 2011 with English language translation.
Japanese Office Action dated Oct. 24, 2011 from corresponding Japanese Patent Application Publication No. 2007-119305 together with partial English language translation.

(Continued)

*Primary Examiner* — Linda Dvorak
*Assistant Examiner* — Amanda Scott
(74) *Attorney, Agent, or Firm* — Scully, Scott, Murphy & Presser, P.C.

(57) ABSTRACT

An endoscopic instrument includes: a high-frequency knife for carrying out incisional intervention; a wire having a distal end connected to the high-frequency knife; an outer sheath for allowing the wire to pass therethrough; a main body having a proximal end of the sheath fixed thereto; a first slider, capable of freely sliding on the main body, having the wire fixed thereto; at least a stopper projecting radially outward relative to the wire; a first abutment member making contact with the stopper and regulating distal sliding movement of the wire; and a projection-length-adjusting member, provided in the outer sheath, for regulating proximal sliding movement of the wire by making contact with the stopper. This configuration allows the high-frequency knife to be maintained at different projection lengths based on the stopper making contact with the first abutment member and the stopper making contact with the projection-length-adjusting member.

5 Claims, 9 Drawing Sheets

FOREIGN PATENT DOCUMENTS

| | | |
|---|---|---|
| JP | A 2000-342594 | 12/2000 |
| JP | 2004-544 | 1/2004 |
| JP | 2004-154485 A | 6/2004 |
| JP | A 2004-167081 | 6/2004 |
| JP | 2005-503863 A | 2/2005 |
| JP | 2006-326157 A | 12/2006 |
| WO | WO 03/026524 A2 | 4/2003 |
| WO | WO 03/26524 A2 | 4/2003 |

OTHER PUBLICATIONS

Japanese Office Action dated Oct. 25, 2011 from corresponding Japanese Patent Application No. 2007-119305 together with partial English language translation.

* cited by examiner

ENDOSCOPIC INSTRUMENT

BACKGROUND OF THE INVENTION

1. Field of the Invention

The present invention relates to an endoscopic instrument inserted into an operation channel of an endoscopic apparatus.

The present application claims priority to Japanese Patent Application No. 2007-119305 filed Apr. 27, 2007, the content of which is incorporated herein by reference.

2. Background Art

Conventionally known instruments, e.g., needle knives endoscopically inserted into a body cavity, incise mucosa, etc. using high-frequency electric current (see Japanese Unexamined Utility Model (Registration) Application Publication No. S61-191012, hereinafter called Patent Document 1). Instruments of this type have an incising section, e.g., an interventional needle knife disposed on a distal end of a wire inserted into an insulative sheath inserted through an endoscope channel. The incising section is capable of freely projecting or retracting relative to the distal end of the sheath by maneuvering a maneuvering member having a proximal end of the wire attached thereon.

The projection length, which is generally short, of the incising section of the aforementioned instrument cannot be adjusted easily. Also, in many cases, the maneuvering amount of the maneuvering member does not correspond to the projecting/retracting amount of a distal end member equally since the endoscope inserted into a body cavity makes complex curves. This enables only a two-step adjustment of the incising section, i.e., a full projection state and a full retracted state, into a sheath under present circumstances.

An endoscopic incision instrument proposed for solving the problem has an engagement section having a greater diameter than an inner diameter of a sheath disposed on an electrode or a maneuvering section located in the sheath. This enables fine adjustment of the projection length by means of preload applied when extending or retracting the incising section (see Japanese Unexamined Patent Application, First Publication No. 2004-544, hereinafter called Patent Document 2). However, adjusting the projection length of the incising section by the incision instrument proposed in Patent Document 2 necessitates the observation of an image of the distal end picked up by the endoscope distally slantwise. By using the above method, it is difficult to reliably obtain a desirable projection length reliably since the projection length is generally subject to a small pitch, e.g., 0.5 mm etc.

The present invention was conceived in consideration of the aforementioned circumstances, and an object thereof is to provide an endoscopic instrument that can easily and reliably adjust and maintain two or more stepwise projection length of the incising section relative to a sheath.

SUMMARY OF THE INVENTION

A first aspect of the present invention is an endoscopic instrument which includes: an incising section inserted into a body cavity endoscopically for carrying out incisional intervention; a wire having a distal end connected to the incising section; a sheath, made from insulative material, for allowing the wire to pass therethrough; a main body having a proximal end of the sheath fixed thereto; a wire-maneuvering section, having a proximal end of the wire fixed thereto, capable of freely sliding in an axial line direction of the main body; at least a stopper, provided to the incising section or the wire, for projecting radially outward relative to the wire; a distal-regulation section, provided to the sheath, for regulating proximal sliding movement of the wire by making contact with the stopper; and a proximal-regulating section, provided in the sheath, for regulating proximal sliding movement of the wire by making contact with the stopper, wherein different projection lengths of the incising section can be maintained when the stopper makes contact with the distal-regulation section and when the stopper makes contact with the proximal-regulating section.

Note that, in the present invention, "proximally" or "proximal end" indicates where a slider, which will be explained later, is disposed with respect to a sliding direction of the wire; and "distally" or "distal end" indicates where the incising section is disposed.

The endoscopic instrument according to the present invention reliably maintains a specific projection length of the incising section projecting from the sheath by maneuvering the wire-maneuvering section so that the stopper abuts to the distal-regulation section. A projection length, which is different from the aforementioned specific projection length, of the incising section projecting from the sheath is reliably maintained by maneuvering the wire-maneuvering section so that the stopper abuts the distal-regulation section.

The endoscopic instrument according to the present invention may further include: a maneuvering sheath, disposed in the sheath, for allowing the distal end of the wire to pass therethrough; and a sheath-maneuvering section, disposed slidably in an axial line direction of the main body, having the proximal end of the sheath fixed thereto, wherein the distal-regulation section may be provided to the distal end of the sheath, and the proximal-end-regulating section may be provided to a distal end of the maneuvering sheath.

In addition, the endoscopic instrument according to the present invention may further include: a maneuvering sheath, disposed in the sheath, for allowing the distal end of the wire to pass therethrough; and a sheath-maneuvering section, disposed slidably in an axial line direction of the main body, having the proximal end of the sheath fixed thereto, wherein the distal-regulation section and the proximal-end-regulating section may be provided to distal ends of a pair of elastic members provided to the distal end of the maneuvering sheath and urged radially outward relative to the maneuvering sheath.

A second aspect of the present invention is an endoscopic instrument which includes: an incising section inserted into a body cavity endoscopically for incisional intervention; a wire having a distal end connected to the incising section; a sheath, made from insulative material, for allowing the wire to pass therethrough; a main body having a proximal end of the sheath fixed thereto; a wire-maneuvering section, having a proximal end of the wire fixed thereto, capable of freely sliding in an axial line direction of the main body; at least a stopper, provided to the incising section or the wire, for projecting radially radially outward relative to the wire; and at least two engagement sections, provided to the sheath and disposed with interval in longitudinal direction of the wire, for maintaining a predetermined position of the wire by engaging with the stopper, wherein different projection lengths of the incising section can be maintained based on the stopper making contact with each engagement section.

A third aspect of the present invention is an endoscopic instrument which includes: an incising section inserted into a body cavity endoscopically for incisional intervention; a wire having a distal end connected to the incising section; a sheath, made from insulative material, for allowing the wire to pass therethrough; a main body having a proximal end of the sheath fixed thereto; a wire-maneuvering section, having a proximal end of the wire fixed thereto, capable of freely sliding in an axial line direction of the main body; a stopper, provided to the incising section or the wire, for projecting radially outward relative to the wire; a distal-regulation section, provided to the sheath, for regulating a proximal sliding movement of the wire by making contact with the stopper; and a balloon, disposed between the distal-regulation section and the stopper, capable of dilating and contracting, wherein the different projection lengths of the incising section can be maintained based on dilated state of the balloon and on contracted state of the balloon.

The endoscopic instrument according to the present invention can easily and reliably adjust and maintain two or more stepwise projection lengths of the incising section relative to a sheath. Therefore, the incising section having appropriately adjusted projection length can be used for intervention in accordance with tissue or site of incision object and in accordance with angles of the incising section making contact with the incision object tissue.

BRIEF DESCRIPTION OF DRAWINGS

FIGS. 5A to 8C illustrate tissue-collecting movement of the endoscopic instrument.

PREFERRED EMBODIMENTS

An endoscopic instrument (simply hereinafter called an instrument) according to a first embodiment of the present invention will be explained with reference to FIGS. 1 to 6.

Figure 1:
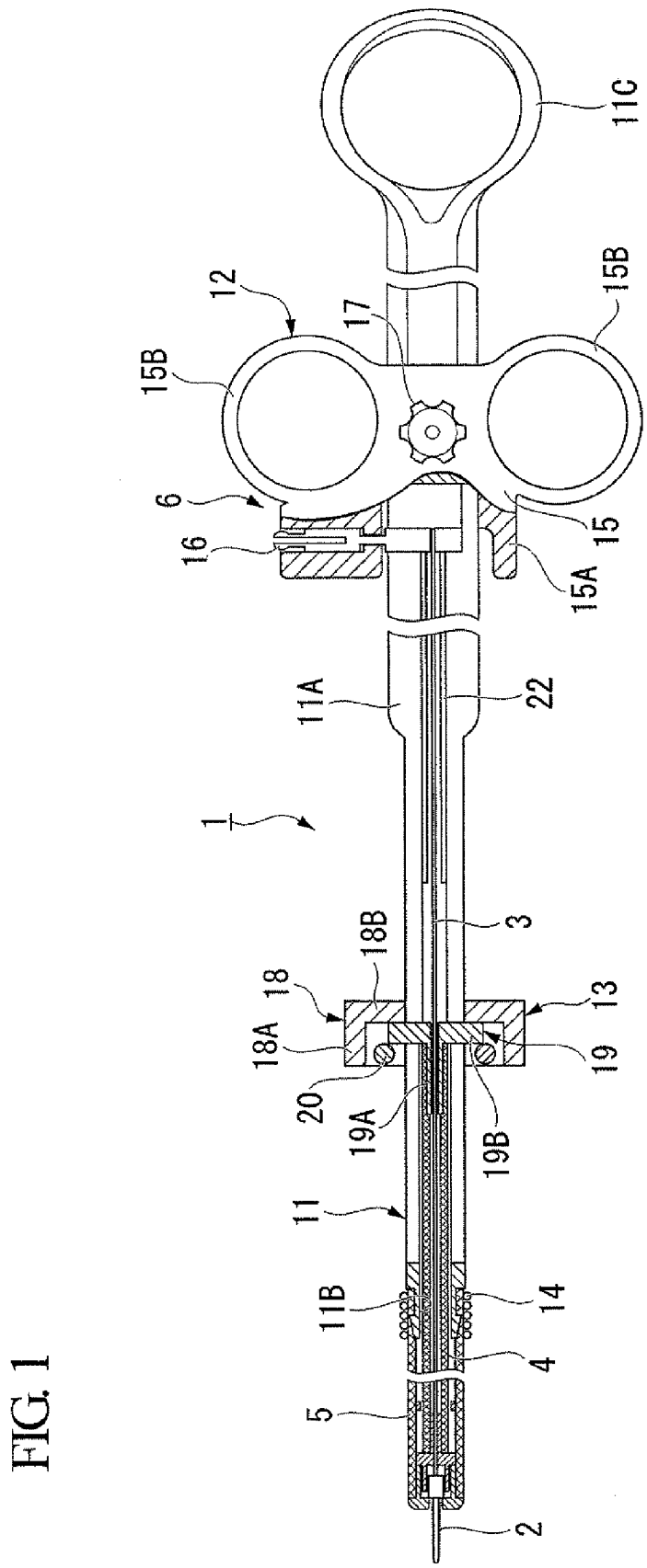
FIG. 1 is a cross-sectional view showing an endoscopic instrument according to a first embodiment of the present invention.

FIG. 1 is a cross-sectional view showing an instrument 1 of the present embodiment. The instrument 1 includes a wire 3 having a high-frequency knife (incising section) 2 attached to the distal end thereof; an inner sheath (maneuvering sheath) 4 that covers the outer periphery of the wire 3; an outer sheath (sheath) 5 that covers the outer periphery of the inner sheath 4; and a maneuvering section 6 for maneuvering the wire 3 and the inner sheath 4.

The high-frequency knife (simply hereinafter called knife) 2 made of a metal bar having a length of 3 mm etc. is subject to high-frequency power supply to carry out incisional intervention for coelomic tissue as explained later. The knife 2 may have a pad shape or hook shape in place of a bar shape.

The wire 3 made of metal, e.g., stainless steel is inserted through the inner sheath 4 that will be explained later. As illustrated in an enlarged view in FIG. 2, a stopper 7 having a projecting section 7A projecting radially outward relative to the knife 2 is provided between the distal end of the wire 3 and the proximal end of the knife 2.

The stopper 7 may be provided to the knife 2 or to the wire 3. Alternatively, the stopper 7 may have the projecting section 7A a part of which projects radially outward. Yet alternatively, the projecting section 7A of the stopper 7 may be a cylinder having a diameter greater than the diameter of the knife 2.

The insulative and elastic inner sheath 4 is a tubular member made of resin etc. Fixed to the distal end (end section in the vicinity of the knife 2) of the inner sheath 4 by using a press-fitting method is a projection-length-adjusting member (proximal-regulating section) 8 which regulates a distal sliding movement of the wire 3 and adjusts the projection length of the knife 2.

The projection-length-adjusting member 8 has a through-hole 8A which allows the wire 3 to pass therethrough; a cylinder section 8B having an inner diameter greater than that of the projecting section 7A of the stopper 7; and a flange section 8C provided between the cylinder section 8B and the distal end of the inner sheath 4. The projection section 7A of the stopper 7 upon retracting the wire 3 as explained later is configured to move up to the proximal end of the cylinder section 8B since the inner diameter of the through-hole 8A is set to be smaller than the outer diameter of the projecting section 7A.

Similarly to the inner sheath 4, the outer sheath 5 is an insulative and elastic tubular member. The outer sheath 5 having an inner diameter greater than the outer diameter of the inner sheath 4 allows the inner sheath 4 to pass therethrough. Fixed to the distal end of the outer sheath 5 by using press-fitting method is a first abutment member (distal-regulation section) 9 having a through-hole 9A that allows the knife 2 to pass therethrough. A second abutment member 10 projecting radially inward with respect to the outer sheath 5 is fixed inside of the outer sheath 5 by using a press-fitting method distally relative to a first abutment member 9.

The first abutment member 9 has a distal end section 9B having the through-hole 9A thereinside; and a cylinder section 9C press-fitted into the outer sheath 5. The stopper 7 upon extending the wire 3 as explained later is configured to not move across the distal end section 913 since the inner diameter of the through-hole 8A is set to be smaller than the outer diameter of the projecting section 7A.

The second abutment member 10 formed by an O-ring, etc. is fixed at a position that permits movement of the flange section 8C by e.g., 0.5 millimeters from an end surface 9D of the cylinder section 9C of the first abutment member 9. The projection-length-adjusting member 8 is configured not to move across the second abutment member 10 since the second abutment member 10 is configured to abut the flange section 8C of the projection-length-adjusting member 8.

FIG. 1 shows the configuration in which the maneuvering section 6 is provided with a main body 11 having the outer sheath 5 fixed thereto; a first slider (wire-maneuvering section) 12 having the wire 3 fixed thereto; and a second slider (sheath-maneuvering section) 13 having the inner sheath 4 fixed thereto.

The main body 11 is a bar-shaped member having a guide groove 11A extending in an axial direction for sliding the first slider 12 and the second slider 13. Provided to the distal end of the main body 11 is a through-hole 11B for allowing the wire 3 and the inner sheath 4 to pass therethrough, and the proximal end of the outer sheath 5 is fixed to the distal end of the main body 11 by fixing means, e.g., a coil 14. Provided to the proximal end of the main body 11 is a finger hook ring 11C for operation.

The first slider 12 is provided with a first maneuvering member 15 having a cylinder section 15A that surrounds the outer periphery of the main body 11; and a plug 16, connected to a high-frequency power supply which is not shown in the drawings, attached to the first maneuvering member 15. The proximal end of the wire 3 is inserted through a buckling-preventive pipe 22 made of rigid material.

The proximal end of the wire 3 and the proximal end of the buckling-preventive pipe 22 are connected and fixed to the plug 16 in the guide groove 11A by fixing means, e.g., screws not shown in the drawing. That is, the first slider 12 and the wire 3 are attached to the main body 11 and are capable of freely sliding in an axial direction along the guide groove 11A.

In addition, the first maneuvering member 15 is provided with a finger hook handle 15B for operation; and a fixture dial 17 for fixing the first maneuvering member 15 at an arbitrary position on the main body. The first maneuvering member 15 may be fixed to the main body 11 by forming a pair of engageable shapes at arbitrary positions of the main body 11 and the first maneuvering member 15 in place of the fixture dial 17.

The second slider 13 is provided with a second maneuvering member 18 having a cylinder section 18A surrounding the outer periphery of the main body 11 and a bottom surface 18B; and a sliding member 19 fixed to the second maneuvering member 18.

The sliding member 19 has a cylinder section 19A and a fixture section 19B. The cylinder section 19A is fixed to the proximal end of the inner sheath 4 by press-fitting method. The fixture section 19B projecting outward relative to the guide groove 11A is placed and fixed between the bottom surface 18B by fixing means, e.g., a screw 20. That is, the second slider 13 and the inner sheath 4 are attached to the main body 11 and are capable of freely sliding within a specific range along the guide groove 11A.

Operations in using the endoscopic instrument 1 having the previously explained configuration will be explained as follows.

In the beginning, the insertion section of an endoscope is inserted into the body cavity of a patient, etc., and the distal end of the insertion section is moved to the vicinity of an object tissue for intervention.

Subsequently, the first slider 12 and the second slider 13 of the instrument 1 are fully retracted proximally (toward the ring 11C) to dispose the distal end of the instrument 1 corresponding to a third formation as explained later. The distal end of the outer sheath 5 is inserted from a forceps port 101 opening on a maneuvering section of the endoscope 100 into an operation channel 102 illustrated in FIG. 5, and then the distal end of the instrument 1 is projected from the distal end of the insertion section 103. Subsequently, an electric power cord, not shown in the drawing, is connected to the plug 16. The electric power cord may be connected prior to insertion of the instrument 1 into the endoscope 100.

A user adjusts the projection length of the knife 2 by maneuvering the first slider 12 and the second slider 13 to obtain a desirable length thereof. The projection length of the instrument 1 is adjustable in three steps, i.e., 2.0 millimeter, 1.5 millimeter, and 1.0 millimeter.

Figure 2:
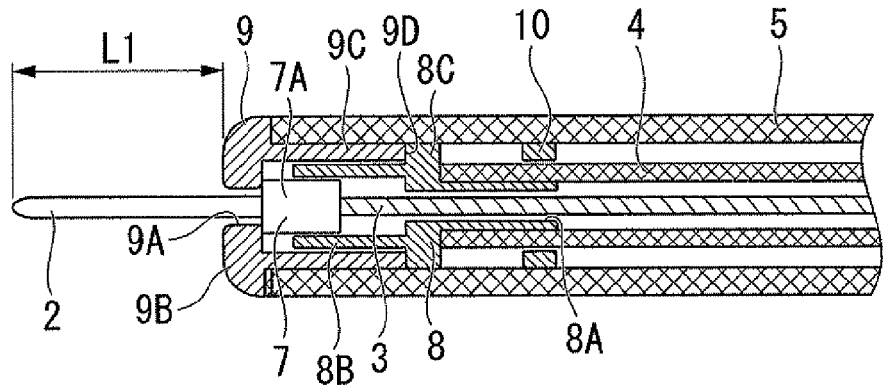
FIG. 2 is an enlarged view of a first formation of the distal end of the endoscopic instrument.

FIG. 2 shows a first formation in which the knife 2 has a 2.0 millimeter of projection length L1.

Extending of the first slider 12 and the second slider 13 pushed by the user causes the flange section 8C of the projection-length-adjusting member 8 provided to the distal end of the inner sheath 4 to abut the proximal end surface of the cylinder section 9C of the first abutment member 9. The second slider 13 stops at that position. Distal sliding movement of the wire 3 is regulated at the corresponding position where the stopper 7 abuts the proximal end surface of the distal end section 9B of the first abutment member 9, and accordingly, the first slider 12 stops. This is a first formation which maintains a 2.0 millimeter of projection length L1.

Instead of the aforementioned operation, extending the first slider 12 alone until being stopped can adjust projection length of the knife 2 to 2.0 millimeter since the stopper 7 abuts the first abutment member 9.

Figure 3:
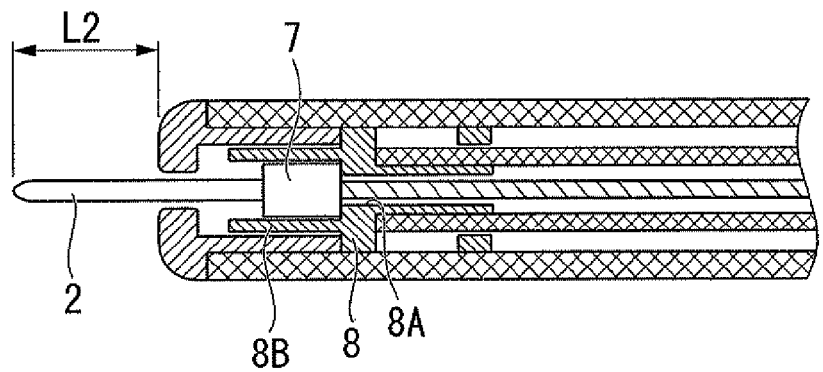
FIG. 3 is an enlarged view of a second formation of the distal end of the endoscopic instrument.

FIG. 3 shows a second formation in which the knife 2 has a 1.5 millimeter of projection length L2.

Moving from the aforementioned first embodiment to the second formation necessitates that the first slider 12 alone is retracted and pulled proximally while the second slider 13 is fixed by the user. Accordingly, the stopper 7 sliding and retracting in the cylinder section 8B of the projection-length-adjusting member 8 makes contact with the proximal end surface of the cylinder section 8B having the through-hole 8A thereon, and stops since proximal sliding movement of the wire 3 is regulated. This is a second formation which maintains 1.5 millimeters of projection length L2.

Figure 4:
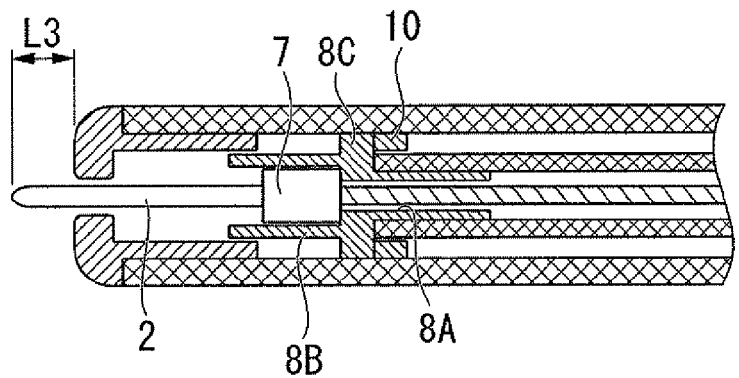
FIG. 4 is an enlarged view of a third formation of the distal end of the endoscopic instrument.

FIG. 4 shows a third formation in which the knife 2 has 1.0 millimeter of a projection length L3. Retracting of the first slider 12 and the second slider 13 proximally by the user causes the first slider 12 to stop since the stopper 7 abuts the proximal end surface of the cylinder section 8B having the through-hole 8A thereon similarly to the second formation. The second slider 13 stops at a position where the flange section 8C abuts the proximally disposed second abutment member 10. This is a third formation which maintains 1.0 millimeter of the projection length L3.

Subsequent to the aforementioned maneuvering, i.e., the projection length adjustment for the knife 2 to a desirable length and fixing the first slider 12 by using the fixture dial 17 if necessary, the user charges a high-frequency electric current to the knife 2 and conducts incisional or dissectional intervention on the object tissue.

The instrument 1 according to the present embodiment extending or retracting at least one of the first slider 12 and the second slider 13 can adjust the projection length of the knife 2 and maintain three different stepwise controls thereof easily and reliably. Therefore, intervention corresponding to the shape of an object tissue can be conducted by desirably adjusting the projection length of the knife 2.

The present invention is not limited to the present embodiment showing an example having the second abutment member 10. The present invention may be free from the second abutment member 10. In this case, the projection length of the knife 2 the adjustable to two steps, i.e., the first formation and the second formation allows the knife 2 to be enclosed fully in the outer sheath 5.

In addition, projection length of the knife 2 not limited to those of the aforementioned forms, can be modified to arbitrary values by changing the dimensions of each component when designed. However, projection length L3 set to have the shortest projection length is preferable to be half the outer diameter of the outer sheath 5 or smaller so as to prevent damaging the wall surface of the operation channel 102 upon inserting the instrument 1 into the endoscope 100.

Figure 6:
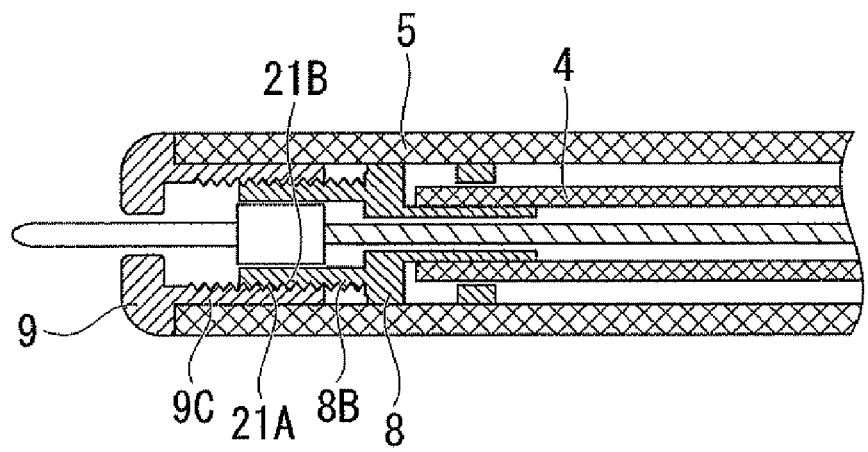
FIG. 6 is an enlarged view showing a modified example of the distal end of the present embodiment.

Furthermore, screw grooves 21A and 21B may be provided on the inner surface of the cylinder section 9C of the first abutment member 9 and the outer surface of the cylinder section 8B of the projection-length-adjusting member 8 as illustrated in a modified example of FIG. 6. This case of the outer sheath 5 capable of rotating around an axial line is fixed to the main body 11 via a rotator, etc. which is not shown in the drawing. This allows the projection-length-adjusting member 8 and the inner sheath 4 to rotate together with the main body 11 while the screw groove 21A engages with the screw groove 21B. Maneuvering this adjustment to the engaging length between the first abutment member 9 and the projection-length-adjusting member 8 permits fine and arbitrary adjustment of the projection length of the knife 2 between the first formation and the second formation.

An instrument according to a second embodiment of the present invention will be explained next with reference to FIGS. 7A to 8.

An instrument 31 according to the present embodiment is different from the endoscopic instrument 1 according to the aforementioned first embodiment in that a projection-length-adjusting member serves as a grasping forceps, and stoppers are different in number and shape. Note that components that are in common with those of the aforementioned endoscopic instrument 1 will be assigned the same numeric symbols and redundant explanations thereof will be omitted.

Figure 7:
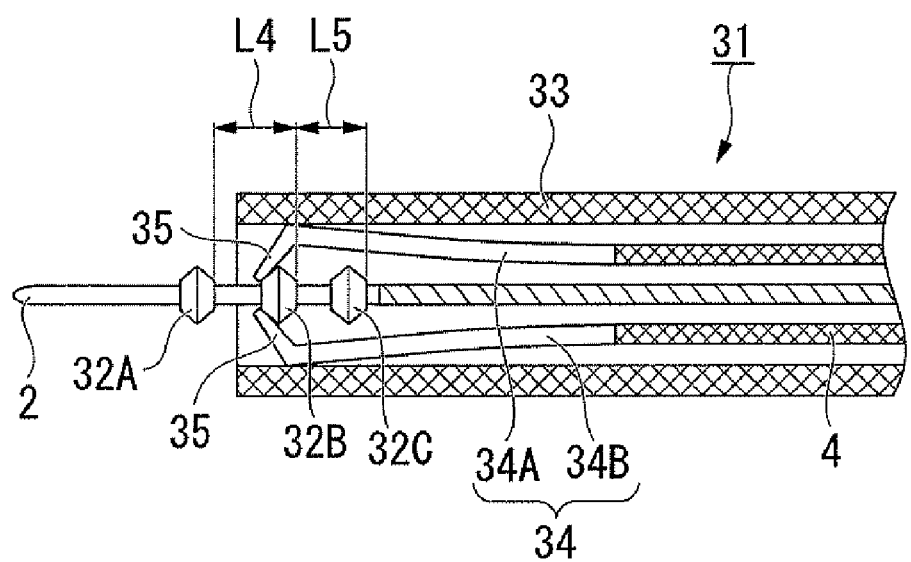
FIG. 7 is an enlarged view showing the distal end of an endoscopic instrument according to a second embodiment of the present invention.
Figure 8A:
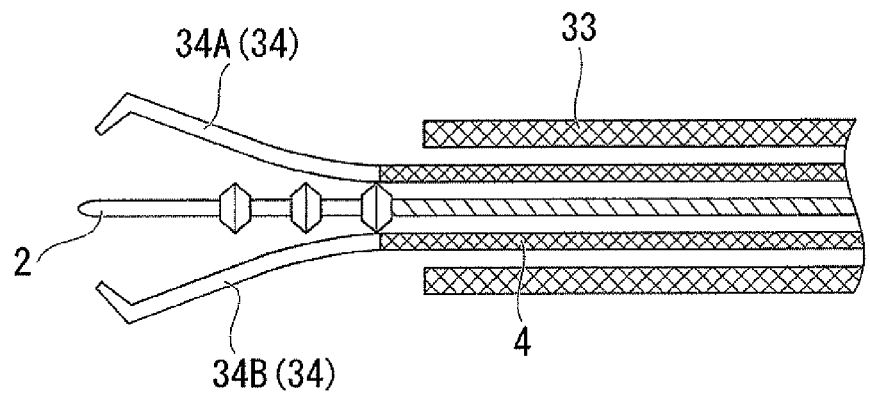

FIG. 7 is an enlarged view of the vicinity of the distal end of the instrument 31. FIG. 7 illustrates three stoppers 32A, 32B, and 32C made of elastic material disposed separately in the longitudinal direction of the wire 3 in the instrument 31. Each stopper has two tapered portions with respect to the longitudinal direction of the knife 2 like a bead of an abacus. Each stopper undergoes different coloration, e.g., red, blue, or yellow etc. Regular pitches set for L4 and 15 between successive two stoppers are 0.5 millimeter etc.

In addition, an outer sheath 33 made of transparent material permits visual recognition of the stoppers 32A, 32B, and 32C from the outside of the outer sheath 33.

Fixed to the distal end of the inner sheath 4 is a grasping forceps 34 including a pair of plate springs (elastic members) 34A and 34B. Each plate spring urged to expand radially outward relative to the outer sheath 33 makes contact with the inner wall of the outer sheath 33. In addition, the distal end of each plate spring is folded radially inward relative to the inner sheath 4 to form a jaw section 35. Functions of the distal-regulation section and the proximal-regulating section are integrated in the jaw section 35 of the instrument 31. Note that three or more plate springs may constitute the grasping forceps 34.

A slide-preventive stopper, not shown in the drawing, provided in the guide groove 11A of the main body 11 and projecting between the second slider 13 and the first slider 12 prevents the second slider 13 from retracting across the slide-preventive stopper. The position of the slide-preventive stopper for enabling a tissue-collecting operation that will be explained later is set to allow the grasping forceps 34 to be fully enclosed in the outer sheath 33 upon abutting the sliding member 19 of the second slider 13 to the slide-preventive stopper.

Operations in using the instrument 31 having the previously explained configuration will be explained.

In the beginning, an endoscope is maneuvered similarly to the first embodiment to be inserted into a body of a patient etc., and the distal end of the instrument 31 is inserted from the forceps port 101 to project from the distal end of the insertion section 103.

A user, in an attempt to adjust the projection length of the knife 2, retracts the second slider 13 proximally to abut to the slide-preventive stopper, which is not shown in the drawing. Sliding this state of first slider 12 distally and proximally obtains a desirable projection length of the knife 2. The third formation indicating the shortest projection length of the knife 2 as illustrated in FIG. 7 is obtained by slightly retracting the first slider 12 upon causing the elastically deforming stopper 32A to distally override the jaw section 35 of the grasping forceps 34 and abutting the proximal end of the stopper 32A to the jaw section 35. The stopper 32A is positioned to maintain a 1.0 millimeter projection length of the knife 2 in the third formation etc.

Maneuvering similarly, i.e., abutting the proximal end of the stopper 32B to the jaw section 35 causes the knife 2 to shift to the second formation that maintains a 1.5 millimeter of projection length. In addition, abutting the proximal end of the stopper 32C to the jaw section 35 causes the knife 2 to shift to the first formation that maintains the longest, i.e., a 2.0 millimeter projection length. The coloration and number of the stoppers observed from the outside of the outer sheath 33 allows the user to recognize with ease as to which formation the distal end of the instrument 31 is disposed in.

Collecting tissue etc. dissected by the knife 2 necessitates a separation of the distal end of the instrument 31 temporally from the tissue; maneuvering the first slider 12 and the second slider 13; and extending the knife 2 and the grasping forceps 34. The plate springs 34A and 34B having the aforementioned urging force expand radially outward upon projecting the grasping forceps 34 from the outer sheath 33. Pulling this state of the first slider 12 proximally causes the retracted knife 2 to be enclosed in the outer sheath 33.

Figure 8B:
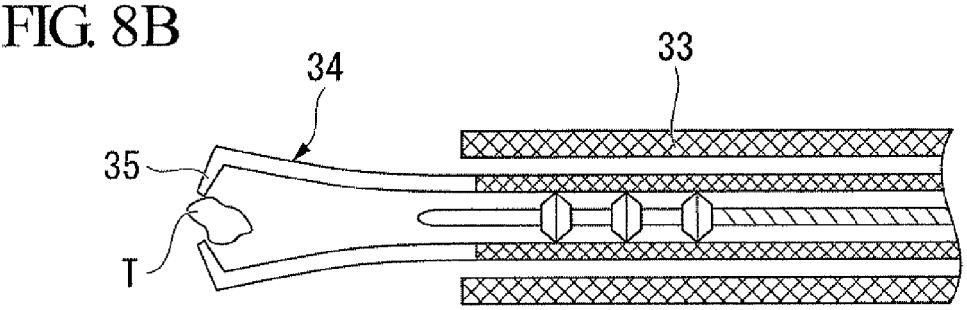
Figure 8C:
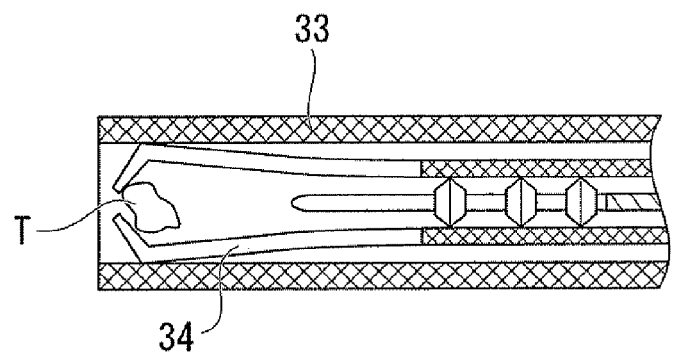

FIG. 8B illustrates moving the grasping forceps 34 to the vicinity of a collection object, i.e., the tissue T; enclosing the grasping forceps 34 from the proximal end into the outer sheath 33 while pulling the second slider 13 proximally; and closing the jaw sections 35 to place the tissue T thereamong. FIG. 8C illustrates enclosing the grasping forceps 34 fully in the outer sheath 33 and collecting the tissue T.

The instrument 31 according to the present embodiment having the grasping forceps 34 in place of the projection-length-adjusting member 8 can collect tissue dissected by the knife 2 without changing instruments.

In addition, the outer sheath 33 made of transparent material and the stoppers 32A, 32B, and 32C each having different coloration allow the user observing the coloration and number of the stoppers from outside of the outer sheath 33 to recognize and adjust the projection length of the knife 2 correctly.

The present embodiment explained with reference to an example in which the grasping forceps 34 are positioned by abutting the second slider to the slide-preventive stopper which is not illustrated in the drawings may be replaced by the positioning configuration according to the aforementioned first embodiment in which the flange structure provided to the inner sheath abuts the distally disposed second abutment member.

An instrument according to a third embodiment of the present invention will be explained next with reference to FIGS. 9 to 12. The difference between an instrument 41 according to the present embodiment from the aforementioned endoscopic instrument 1 is based on the absence of the inner sheath and the second slider, and on the shape of the stoppers.

Note that components that are identical to those of the aforementioned instrument 1 will be assigned the same numeric symbols and redundant explanations thereof will be omitted.

Figure 9:
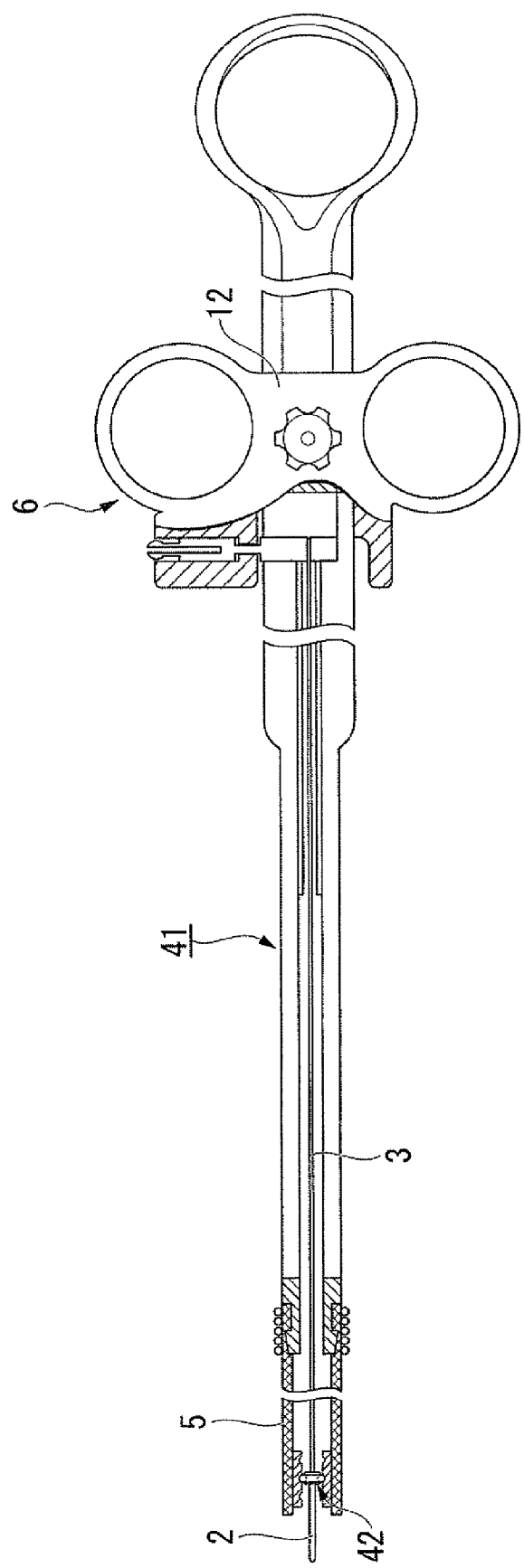
FIG. 9 is a cross-sectional view showing an endoscopic instrument according to a third embodiment of the present invention.

FIG. 9 is a cross-sectional view showing the instrument 41. The instrument 41 acquires a configuration free from the second slider 13 and the inner sheath 4.

Figure 10:
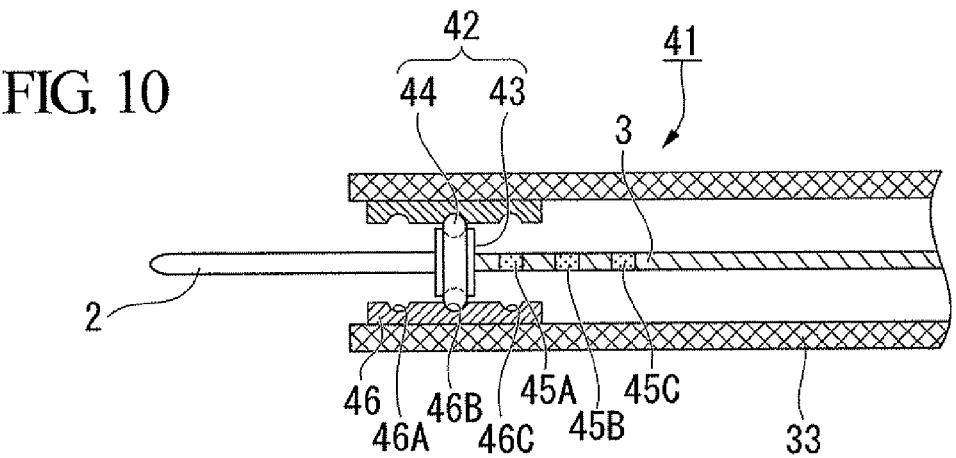
FIG. 10 is an enlarged view of a second formation of the distal end of the endoscopic instrument.

FIG. 10 is an enlarged view of the distal end of the instrument 41. A stopper 42 is provided with a central section 43 connected to the knife 2 and the wire 3; and a annular member 44, e.g., an O-ring attached to the outer periphery of the central section 43.

Provided on the wire 3 are three calibration marks 45A, 45B, and 45C disposed at an interval of 0.5 millimeters etc. in this order from the vicinity of the stopper 42. Each mark undertake different coloration, e.g., red, blue, or yellow, etc. The marks may be modified in number, interval, and coloration in view of distinguishability obtained with respect to first to third formations which will be explained later.

The outer sheath 33 which is equivalent to that of the instrument 31 according to the second embodiment permits visual recognition of the calibration marks 45A, 45B, and 45C from the outside of the outer sheath 33.

Fixed to the distal end of the outer sheath 33 by using a press-fitting method or a welding method is a projection-length-adjusting tube 46 made of elastic material. The inner diameter of the projection-length-adjusting tube 46 smaller than the outer diameter of the stopper 42 is set to allow the knife 2 and the wire 3 to pass therethrough without problem. Formed on the inner surface of the projection-length-adjusting tube 46 are adjustment grooves (engagement sections) 46A, 46B, and 46C disposed at an interval of 0.5 millimeters etc. in the longitudinal direction of the wire 3.

Operations in using the instrument 41 having the aforementioned configuration will be explained as follows.

A user in the beginning pulls the first slider 12 proximally and inserts the distal end of the instrument 41 into the endoscope 100 while the knife 2 is fully enclosed in the outer sheath 33. This state of stopper 42 is disposed more proximally relative to the projection-length-adjusting tube 46.

The first slider 12 having approached an object tissue for intervention is extended to extend the knife 2 and the stopper 42. The stopper 42 having made contact with the proximal end of the projection-length-adjusting tube 46 extends while deforming a proximal part of the adjustment groove 46C elastically. The wire held upon engaging the stopper 42 with the adjustment groove 46C releases the elastic deformation occurring proximally relative to the adjustment groove 46C.

Tactile sense (clicking feeling) at this time is transferred to the first slider 12, and the distal sliding of the wire 3 is regulated. This is the third formation in which the knife 2 has the shortest projection length from the outer sheath 33.

Positions of the projection-length-adjusting tube 46 and the stopper 42 are designed in the third formation so that the knife 2 maintains a projection length of 1.0 millimeter etc. All of the marks 45A, 45B, and 45C disposed proximally relative to the projection-length-adjusting tube 46 in the third formation permit observation from the outside of the outer sheath 33.

The stopper 42 further extended to reach the adjustment groove 46B transfers a clicking feeling to the first slider 12, thereby shifting to the second formation as illustrated in FIG. 10 showing the knife 2 maintaining a projection length of 1.5 millimeters. The calibration mark 45A disposed the most distally positioned in the projection-length-adjusting tube 46 in the second formation cannot be observed from the outside of the outer sheath 33.

Figure 11:
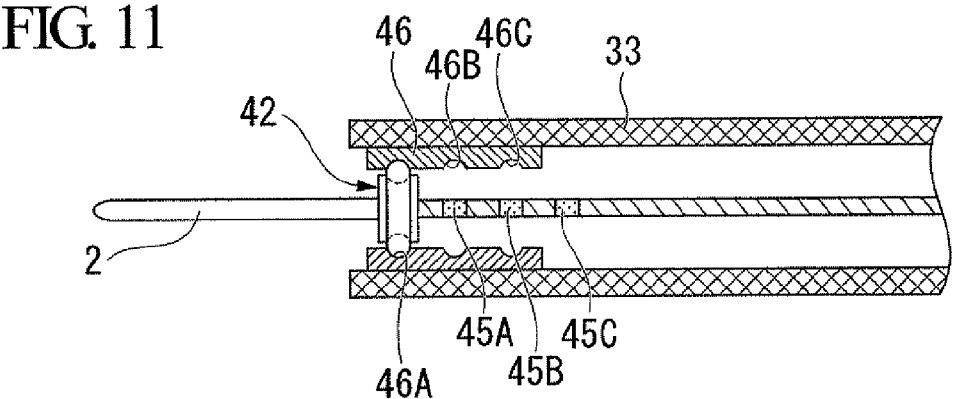
FIG. 11 is an enlarged view of a third formation of the distal end of the endoscopic instrument.

The knife 2 shifts to the first formation that maintains the longest projection length, i.e., 2.0 millimeter as illustrated in FIG. 11 when the stopper 42 reaches the adjustment groove 46A. The second formation permits observation of the calibration mark 45C alone from the outside of the outer sheath 33 since the calibration mark 45B is positioned in the projection-length-adjusting tube 46.

The instrument 41 according to the present embodiment free from the inner sheath 4 and the second slider 13 can acquire a simple structure. In addition, the stopper 42 upon reaching one of the adjustment grooves 46A, 46B, and 46C releases the elastic deformation of the projection-length-adjusting tube 46, thereby transferring a clicking feeling to the first slider 12. Accordingly, the user can recognize each formation shift reliably.

Furthermore, the marks 45A, 45B, and 45C provided on the wire 3 allow the user observing through the outer sheath 33 to recognize reliably as to which formation the distal end of the instrument 41 is disposed based on the number and coloration of the marks.

Figure 12:
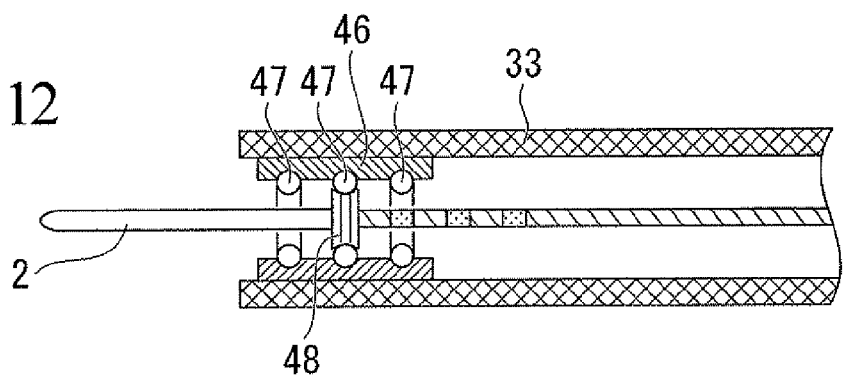
FIG. 12 is an enlarged view showing a modified example of the distal end of the present embodiment.

The present embodiment explained with reference to the example in which the annular members are fixed to the stopper 42 may be replaced by a modified example shown in FIG. 12 illustrating that annular members 47 disposed at a regular interval are fixed onto the projection-length-adjusting tube 46 by using a press-fitting method etc.; and that grooves engaging with the annular members 47 are formed on the outer periphery surface of the stopper 48.

Adjusting the position for fixing the annular members 47 so that this state of stopper 48 positioned between the annular members 47 obtains the first to third formations causes transferring of the clicking feeling to occur synchronously with the shifting of formations.

An instrument according to a fourth embodiment of the present invention will be explained next with reference to FIGS. 13 to 15. The difference between an instrument 51 according to the present embodiment from the aforementioned endoscopic instrument 1 is based on the absence of the inner sheath and the second slider, and presence of a balloon disposed in the vicinity of the outer sheath.

Note that components that are identical to those of the aforementioned instrument 1 will be assigned the same numeric symbol and redundant explanation thereof will be omitted.

Figure 13:
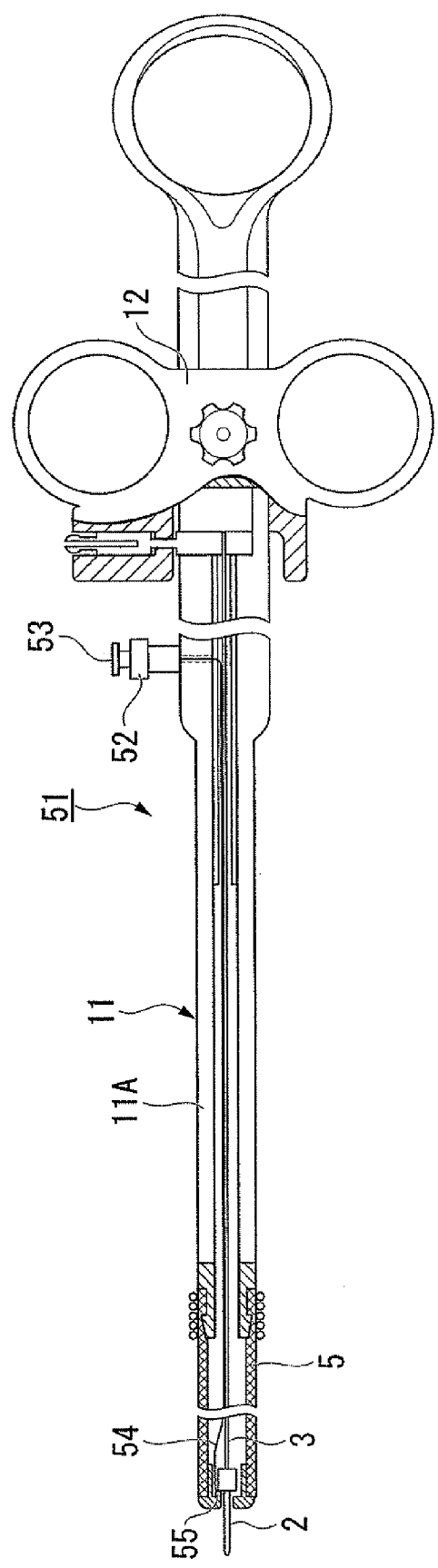
FIG. 13 is a cross-sectional view showing an endoscopic instrument according to a fourth embodiment of the present invention.

FIG. 13 is a front view of an instrument 51. The configuration of the present embodiment free from the second slider 13 and the inner sheath 4 is the same as the instrument 41 of the aforementioned third embodiment. An air-supply mouth piece 52 is attached to the main body 11 of the instrument 51. An air-supply syringe 53 is attached to the air-supply mouth piece 52 hermetically. A commonly known inflator etc. may be connected in place of the syringe 53. The air-supply tube 54 is connected hermetically to the end section in the vicinity of the main body 11 of the air-supply mouth piece 52. The air-supply tube 54 passing through the guide groove 11A is inserted into the outer sheath 5.

Figure 14:
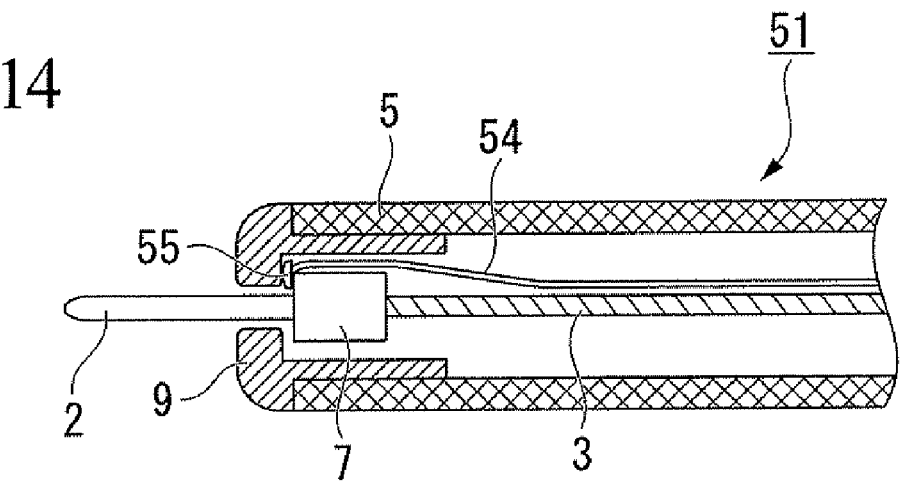
FIG. 14 is an enlarged view showing the distal end of the embodiment.
Figure 15:
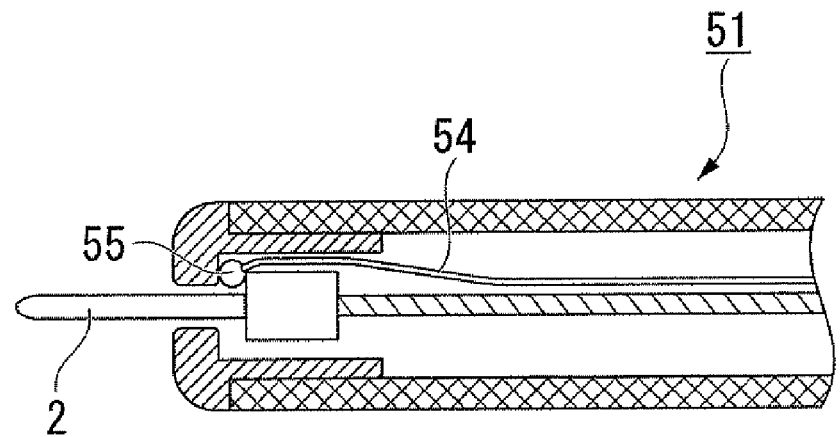
FIG. 15 illustrates the distal end of the endoscopic instrument having a dilated balloon state at the distal end thereof.

FIG. 14 is an enlarged view of the distal end of the instrument 51. A balloon 55 is fixed to the distal end of the air-supply tube 54 disposed in the vicinity of the distal end of the outer sheath 5. The balloon 55 is interposed between the first abutment member 9 and the stopper 7.

A preferable balloon 55 for use may be of so-called compliance type capable of providing correct control to projection length of the knife 2 because dilation diameter of this type has little change based on change in air pressure for dilation. Diameter of the dilated balloon 55 set in the present embodiment is e.g., 0.5 millimeters. Arbitrary diameter may be set for the dilated balloon 55.

Operations in using the instrument 51 having the previously explained configuration will be explained.

FIG. 14 shows that extending the first slider 12 without dilating the balloon 55 to abut the stopper 7 to the first abutment member 9 obtains the first formation where the knife 2 has the longest projection length. The present embodiment sets this state of the knife 2 to maintain a 1.5 millimeter of projection length.

Figure 5:
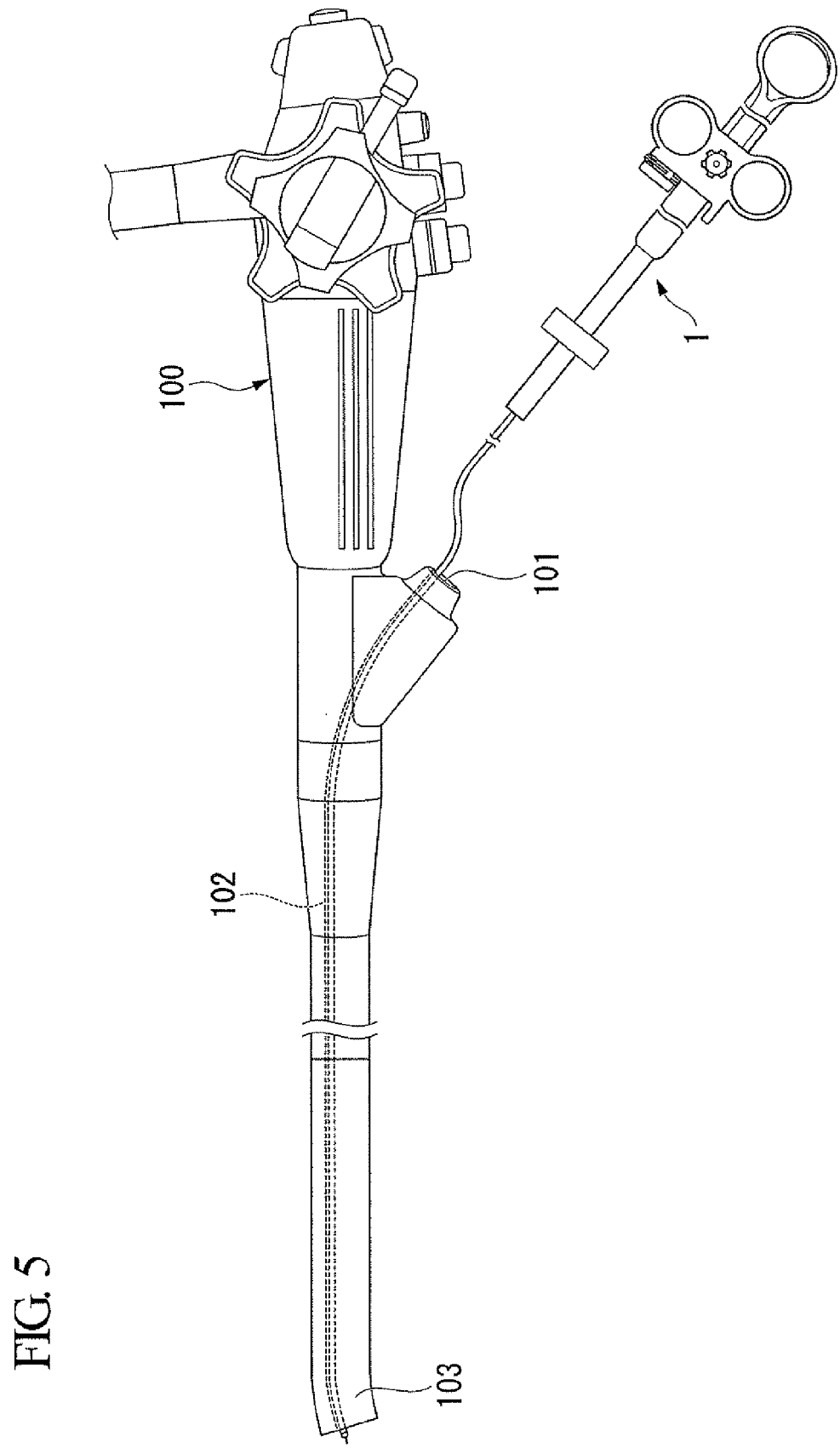
FIG. 5 is a general view showing the endoscopic instrument inserted through an endoscope.

FIG. 5 shows that air supplied from a syringe 53 maneuvered by the user through the air-supply tube 54 to the balloon 55 dilates the balloon 55 between the first abutment member 9 and the stopper 7. This results in the stopper 7 being retracted by 0.5 millimeter which corresponds to the diameter of the balloon 55. This is the second formation which maintains 1.0 millimeter of projection length of the knife 2. That is, the instrument 51 can provide two stepwise control of projection length to the knife 2.

The present embodiment explained with reference to the example showing the balloon 55 interposed between the first abutment member 9 and the stopper 7 may be replaced by a configuration fixing the balloon 55 at an arbitrary position proximal relative to the stopper 7. This case of balloon 55 making contact with the stopper 7 regulates a proximal sliding movement of the knife 2, thereby providing two stepwise controls of projection length to the knife 2.

The technical scope of the present invention is not limited to the embodiments described above. Rather, various modifications may be added without deviating from the spirit of the invention.

The present invention not limited to the aforementioned first embodiment explained with reference to the example provided with the projection-length-adjusting member fixed to the distal end of the inner sheath and may have a configuration having a non-slidable inner sheath fixed to a main body free from a projection-length-adjusting member. Such a case of the inner sheath making contact with the stopper and regulating a proximal sliding movement of the knife can provide two stepwise controls of projection length. Furthermore, a proximal sliding movement of the knife may be regulated by a second abutment member in place of the inner sheath.

The stopper may abut to the first abutment member further proximally in contrast to the aforementioned embodiments explained with reference to the examples showing the stopper abutting the first abutment member in the vicinity of the distal end of the outer sheath. However, the mid point of the outer sheath in many cases bends because an instrument for use is inserted through an endoscope. Therefore, preferably, the stopper should abut to the vicinity of the hardly bending distal end of the outer sheath to provide desirable projection length control.

What is claimed is:

1. An endoscopic instrument comprising:
an incising section inserted into a body cavity endoscopically for carrying out incisional intervention;
a wire having a distal end connected to the incising section;
a sheath, made from insulative material, for allowing the wire to pass therethrough;
a main body having a proximal end of the sheath fixed thereto;
a wire-maneuvering section, having a proximal end of the wire fixed thereto, capable of freely sliding in an axial line direction of the main body;
at least a stopper, provided to the incising section or the wire, for projecting radially outward relative to the wire;
a distal-regulation section, provided to the sheath, for regulating proximal sliding movement of the wire by making contact with the stopper; and
a proximal-regulating section, provided in the sheath, for regulating proximal sliding movement of the wire by making contact with the stopper, wherein
different projection lengths of the incising section can be maintained when the stopper makes contact with the distal-regulation section and when the stopper makes contact with the proximal-regulating section.

2. The endoscopic instrument according to claim 1, further comprising:
a maneuvering sheath, disposed in the sheath, for allowing the distal end of the wire to pass therethrough; and
a sheath-maneuvering section, slidably disposed in an axial line direction of the main body, having the proximal end of the sheath fixed thereto, wherein
the distal-regulation section is provided to the distal end of the sheath, and
the proximal-regulating section is provided to a distal end of the maneuvering sheath.

3. The endoscopic instrument according to claim 1, further comprising:
a maneuvering sheath, disposed in the sheath, for allowing the distal end of the wire to pass therethrough; and
a sheath-maneuvering section, disposed slidably in an axial line direction of the main body, having the proximal end of the sheath fixed thereto, wherein
the stoppers are disposed at intervals in a longitudinal direction of the wire,
the distal-regulation section and the proximal-regulating section are provided to distal ends of a pair of elastic members provided to the distal end of the maneuvering sheath and urged radially outward relative to the maneuvering sheath.

4. An endoscopic instrument comprising:
an incising section inserted into body cavity endoscopically for incisional intervention;
a wire having a distal end connected to the incising section;
a sheath, made from insulative material, for allowing the wire to pass therethrough;
a main body having a proximal end of the sheath fixed thereto;
a wire-maneuvering section, having a proximal end of the wire, capable of freely sliding in an axial line direction of the main body;
a stopper, provided to the incising section or the wire, for projecting radially outward relative to the wire; and
at least two engagement sections, provided to the sheath and disposed with interval in longitudinal direction of the wire, for maintaining a predetermined position of the wire by engaging with the stopper, wherein
different projection lengths of the incising section can be maintained based on the stopper making contact with each engagement section.

5. An endoscopic instrument comprising:
an incising section inserted into a body cavity endoscopically for incisional intervention;
a wire having a distal end connected to the incising section;
a sheath, made from insulative material, for allowing the wire to pass therethrough;
a main body having a proximal end of the sheath fixed thereto;

a wire-maneuvering section, having a proximal end of the wire fixed thereto, capable of freely sliding in an axial line direction of the main body;

a stopper, provided to the incising section or the wire, for projecting radially outward relative to the wire;

a distal-regulation section, provided to the sheath, for regulating proximal sliding movement of the wire by making contact with the stopper; and a balloon, disposed between the distal-regulation section and the stopper, capable of dilating and contracting, wherein different projection lengths of the incising section can be maintained based on a dilated state of the balloon and on a contracted state of the balloon.

* * * * *